US012685800B2

(12) United States Patent
Ramos Perez et al.

(10) Patent No.: US 12,685,800 B2
(45) Date of Patent: Jul. 21, 2026

(54) HYDROGEL COMPOSITIONS AND PREPARATION THEREOF

(71) Applicant: IBERHOSPITEX, S.A., Llica de Vall (ES)

(72) Inventors: Victor Ramos Perez, Llica de Vall (ES); Mario Lopez Moya, Llica de Vall (ES)

(73) Assignee: IBERHOSPITEX, S.A., Llica de Vall (ES)

( * ) Notice: Subject to any disclaimer, the term of this patent is extended or adjusted under 35 U.S.C. 154(b) by 778 days.

(21) Appl. No.: 17/914,502

(22) PCT Filed: Mar. 30, 2021

(86) PCT No.: PCT/EP2021/058281
§ 371 (c)(1),
(2) Date: Sep. 26, 2022

(87) PCT Pub. No.: WO2021/198250
PCT Pub. Date: Oct. 7, 2021

(65) Prior Publication Data
US 2023/0372580 A1 Nov. 23, 2023

(30) Foreign Application Priority Data
Mar. 31, 2020 (EP) .................................... 20382259

(51) Int. Cl.

| | |
|---|---|
| ***A61F 13/00*** | (2024.01) |
| ***A61L 15/60*** | (2006.01) |
| ***A61L 26/00*** | (2006.01) |

(52) U.S. Cl.
CPC ......... *A61L 26/008* (2013.01); *A61L 26/0014* (2013.01); *A61L 26/0066* (2013.01); *A61L 2300/206* (2013.01); *A61L 2300/404* (2013.01)

(58) Field of Classification Search
None
See application file for complete search history.

(56) References Cited

U.S. PATENT DOCUMENTS

| | | | | |
|---|---|---|---|---|
| 2008/0058747 | A1 | 3/2008 | Singh Kainth et al. | |
| 2011/0196060 | A1* | 8/2011 | Askari ................ | A61L 24/0031 424/1.25 |
| 2012/0314185 | A1* | 12/2012 | Bauman ................ | G02B 1/043 977/782 |
| 2013/0195952 | A1* | 8/2013 | Byrne ................. | A61K 9/0051 424/429 |

FOREIGN PATENT DOCUMENTS

| | | | |
|---|---|---|---|
| EP | 0107376 | A1 | 5/1984 |
| EP | 1061089 | B1 | 3/2004 |
| EP | 1550469 | A1 | 7/2005 |
| EP | 1631642 | B1 | 3/2013 |
| JP | S60192717 | A | 10/1985 |
| JP | S61834204 | A | 4/1986 |

OTHER PUBLICATIONS

Hara, O., "Curing Agents for Epoxy Resin", Three Bond Technical News, Issued Dec. 20, 1990, 32, 11 pages.
Standard Test Method for Rubber Property—Durometer Hardness, ASTM D2240-15, Dec. 13, 2019, pp. 1-13.
Biological Evaluation of Medical Devices—Part 1: Evaluation and testing within a risk management process, Standard test method ISO 10993, pp. 1-48.
Kong, et al., Polym. Chem., 2017, DOI: 10.1039/C7PY01136A.
Benes, et al., Methacrylate-based chromatographic media, pp. 1855-1875.
The International Search Report issued in corresponding International Application No. PCT/EP2021/058281; Mailing Date: Jun. 25, 2021.
Asociacion Espanola de Normalizacion y Certificacion, Adhesives for Paper and Board, Packaging and Disposable Sanitary Products. Tack Measurement for Pressure Sensitive Adhesives. Determination of Rolling Ball Tack., Madrid, Spain.

* cited by examiner

*Primary Examiner* — Brian Gulledge
(74) *Attorney, Agent, or Firm* — Chrisman Gallo Tochtrop LLC

(57) ABSTRACT

The present invention refers to a composition comprising: a) a crosslinked hydrophilic polymer containing amino functional groups, and b) a swelling agent, wherein the crosslinked hydrophilic polymer a) is obtainable by reacting a hydrophilic polymer containing amino functional groups with a crosslinking agent which contains at least two epoxide functional groups. The invention also refers to a method for preparing said composition and uses thereof in medical applications.

20 Claims, 6 Drawing Sheets

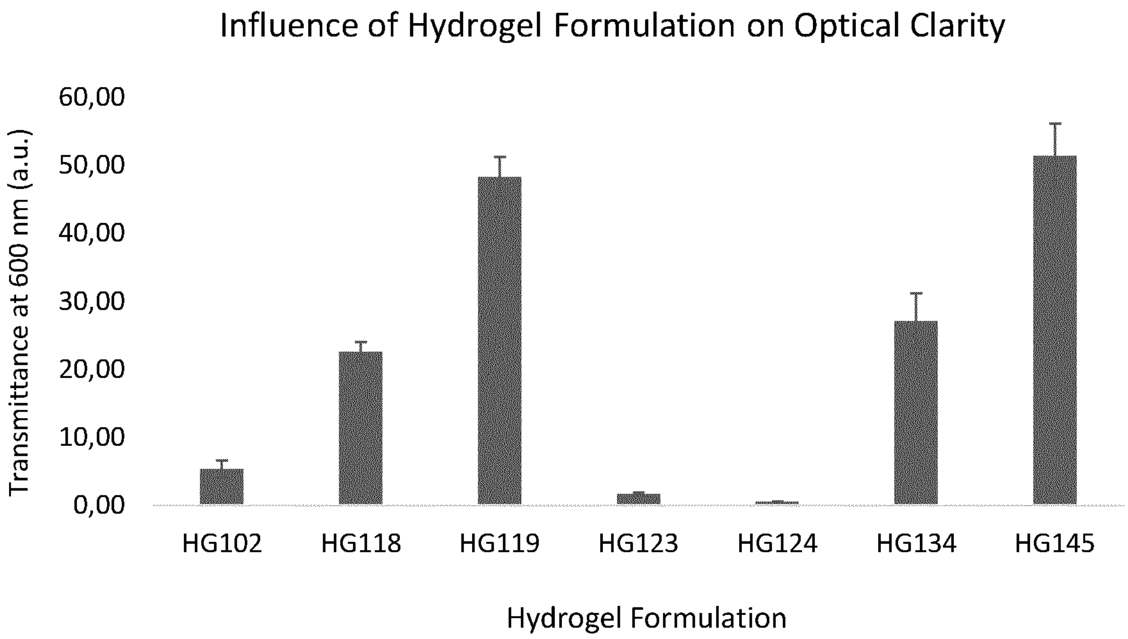
Figura 1A

HG102

HG124

HG118

HG134

HG119

HG145

HG123

HYDROGEL COMPOSITIONS AND PREPARATION THEREOF

This application claims the benefit of European Patent Application EP20382259.8 filed on Mar. 31, 2020.

TECHNICAL FIELD

The present invention refers to compositions in the form of polymeric hydrogels with improved properties for use in articles for medical applications such as dressings, bandages or plasters.

BACKGROUND ART

Hydrogels are crosslinked polymeric networks, which may swell significantly in the presence of aqueous solutions or biological fluids, but do not dissolve and maintain their 3D structure. The high-water content of hydrogels together with their mechanical properties make them attractive for biomedical applications, because they resemble the highly hydrated extracellular matrix of soft tissues. Thus, cross-linked polymeric hydrogels are known for use in medical articles that contact the skin such as, for example, dressings, plasters and drug delivery patches.

Most known hydrogels are polymers made of hydrophilic polymers which have been crosslinked by means of ionizing radiation. Representative examples are provided in EP0107376 and EP1631642. However, use of ionizing radiation requires special equipment and security measures. Moreover, ionizing radiation may be detrimental for a wide variety of the medical articles derived from these polymers due mainly to active principle instability or cross-reactivity with other components of the hydrogel formulation.

Thus, it is desirable to provide alternative methods to obtain hydrogels that do not require radiation-driven cross-linking that are simple, safe and are compatible with active ingredients or other components of the hydrogel formulation.

Currently available hydrogels for wound dressing, medical sealing applications and skin drug delivery devices are colored and/or not fully transparent. This represents a disadvantage for these types of products, for the patient or medical practitioner may not readily inspect the skin lying below. This feature is particularly important for wound dressings and securement dressings, such as catheter securement dressings, for which continued inspection of the wound or catheter below is required in order to avoid complications (infections, phlebitis, etc).

Novel compositions with improved properties, such as enhanced transparency, for manufacture of skin-contacting medical articles are highly desirable.

SUMMARY OF INVENTION

The inventors have developed hydrogel compositions with improved properties when compared to prior art compositions.

The composition of the invention is obtained by mixing a hydrophilic polymer having amino functional groups with a swelling agent and, optionally, other compounds, and a polyepoxide-based crosslinker in a volatile solvent. The process does not require radiation-driven cross-linking, such that it is compatible with a wide range of components, including prophylactically or therapeutically active ingredients contained therein. The resulting product is a crosslinked hydrophilic polymer in the form of a hydrogel, which has good optical clarity that allows direct visualization of the underlaying skin for continuous monitoring. The ingredients used in the composition of the invention are mostly skin-compatible such that a skin-compatible hydrogel is obtained. This product is therefore particularly advantageous for many medical applications, including wound dressing, sealing and drug delivery.

Accordingly, a first aspect of the invention provides a composition comprising: a) a crosslinked hydrophilic polymer containing amino functional groups, and b) a swelling agent, wherein the crosslinked hydrophilic polymer a) is obtainable by reacting a hydrophilic polymer containing amino functional groups with a crosslinking agent, which contains at least two epoxide functional groups. The amino functional groups may be secondary or tertiary amino functional groups.

The composition may comprise additional components, such as modifying polymers, which are compatible with the swelling agent and other active ingredients, such as pharmaceutical or cosmetical active ingredients.

A second aspect of the invention provides a method for obtaining a composition according to the first aspect of the invention, which comprises:

(i) mixing in the presence of a volatile solvent: a) a hydrophilic polymer containing amino functional groups, b) a swelling agent, c) a crosslinking agent which contains at least two epoxide functional groups, (ii) subjecting the mixture at a temperature from 40 to 100° C. during 1 to 24 h, and optionally (iii) placing in an aqueous solution for swelling.

In addition to providing a compound with the intrinsic advantageous properties mentioned above, the process of the invention does not require radiation-driven cross-linking. Avoiding use of radiation is not only advantageous per se, but also because the process is compatible with a wide range of components, including prophylactically or therapeutically active ingredients, which may be included in the final composition without them being in any way adversely affected. Thus, the process of the invention is more versatile, safer and more economical than prior art methods.

A third aspect of the invention provides a product obtainable by the method of the second aspect.

In a fourth aspect, the invention provides for the use of the composition of the first and third aspects for the manufacture of a skin-contact medical article. A fifth aspect provides a skin-contact medical article comprising the composition of the first and third aspects.

The skin-contacting articles of the invention have the advantages mentioned for the composition of the invention as mentioned above, i.e. they are drug-compatible, have good transparency and may be colorless and skin-compatible. As such, these articles allow direct visualization of the underlaying skin for continuous monitoring and are therefore advantageous, for example, as wound dressings and medical sealants. The articles of the invention may also contain drugs, active principles or cosmetic agents and allow delivery and release of such substances at appropriate rates to the skin.

DETAILED DESCRIPTION OF THE INVENTION

Figure 1B:
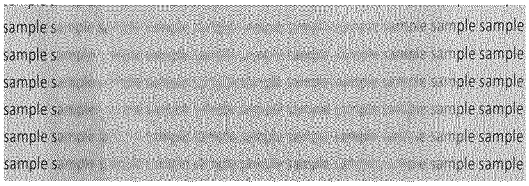
FIG. 1: Optical clarity of hydrogels prepared according to Table 2. 1a: transmittance of 2 mm thick hydrogels determined at a wavelength of 600 nm in a UV/Vis spectrophotometer. 1b: visual determination of optical clarity and color for the 2 mm thick hydrogels.
Figure 1B:
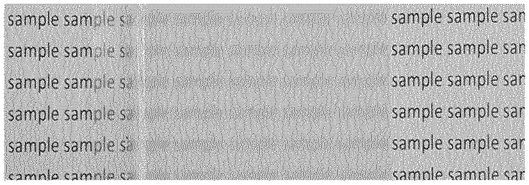
Figure 1B:
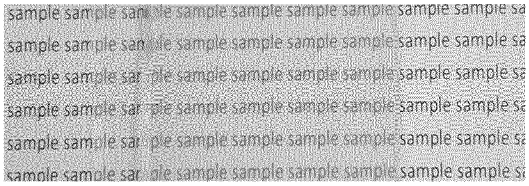
Figure 1B:
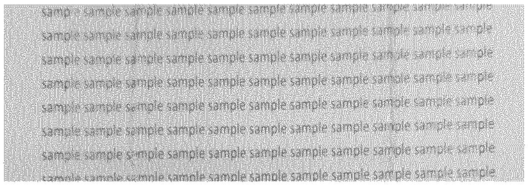
Figure 1B:
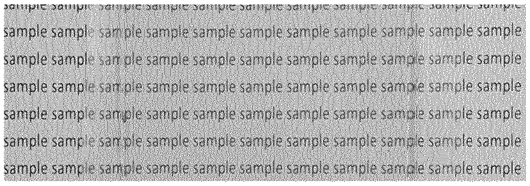
Figure 1B:
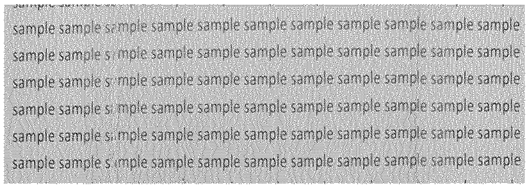
Figure 1B:
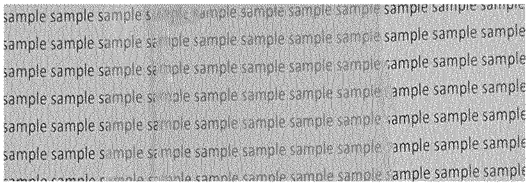
Figure 2:
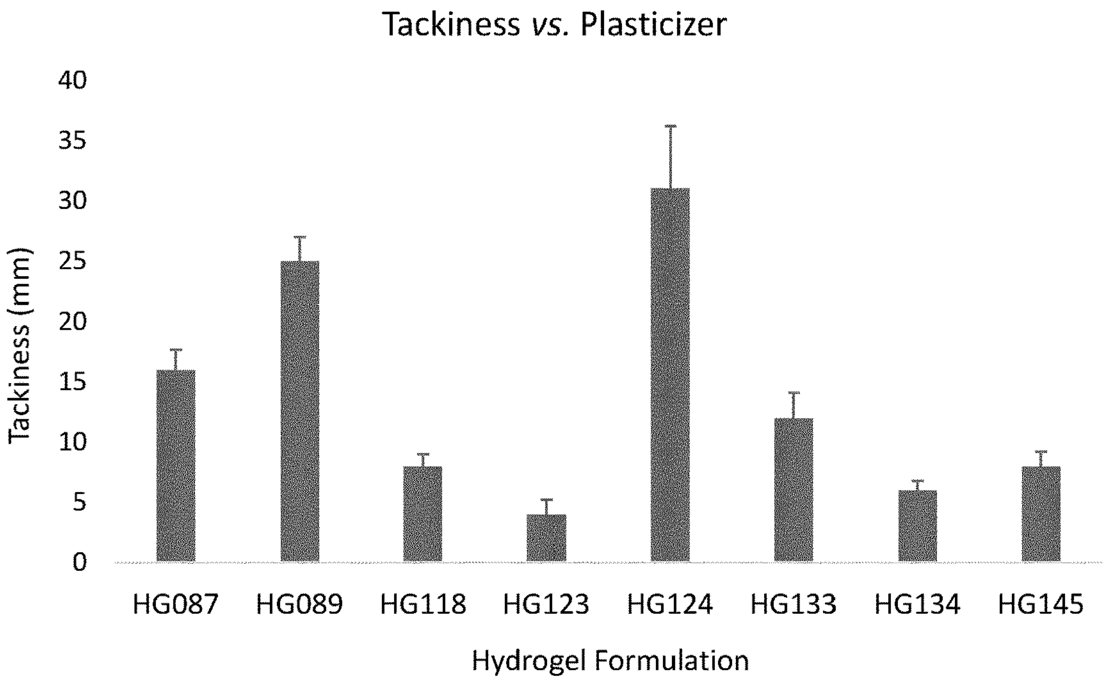
FIG. 2: Influence of plasticizer in the tackiness of hydrogel compositions, prepared according to table 3.
Figure 3:
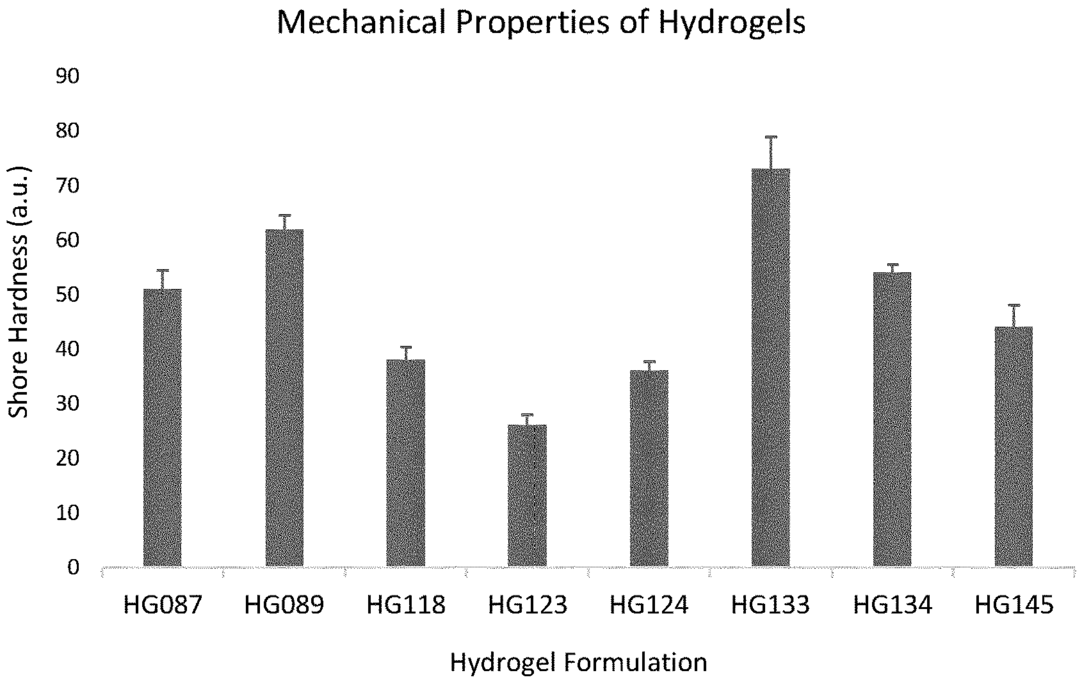
FIG. 3: Shore hardness of hydrogel compositions, prepared according to table 3.
Figure 4:
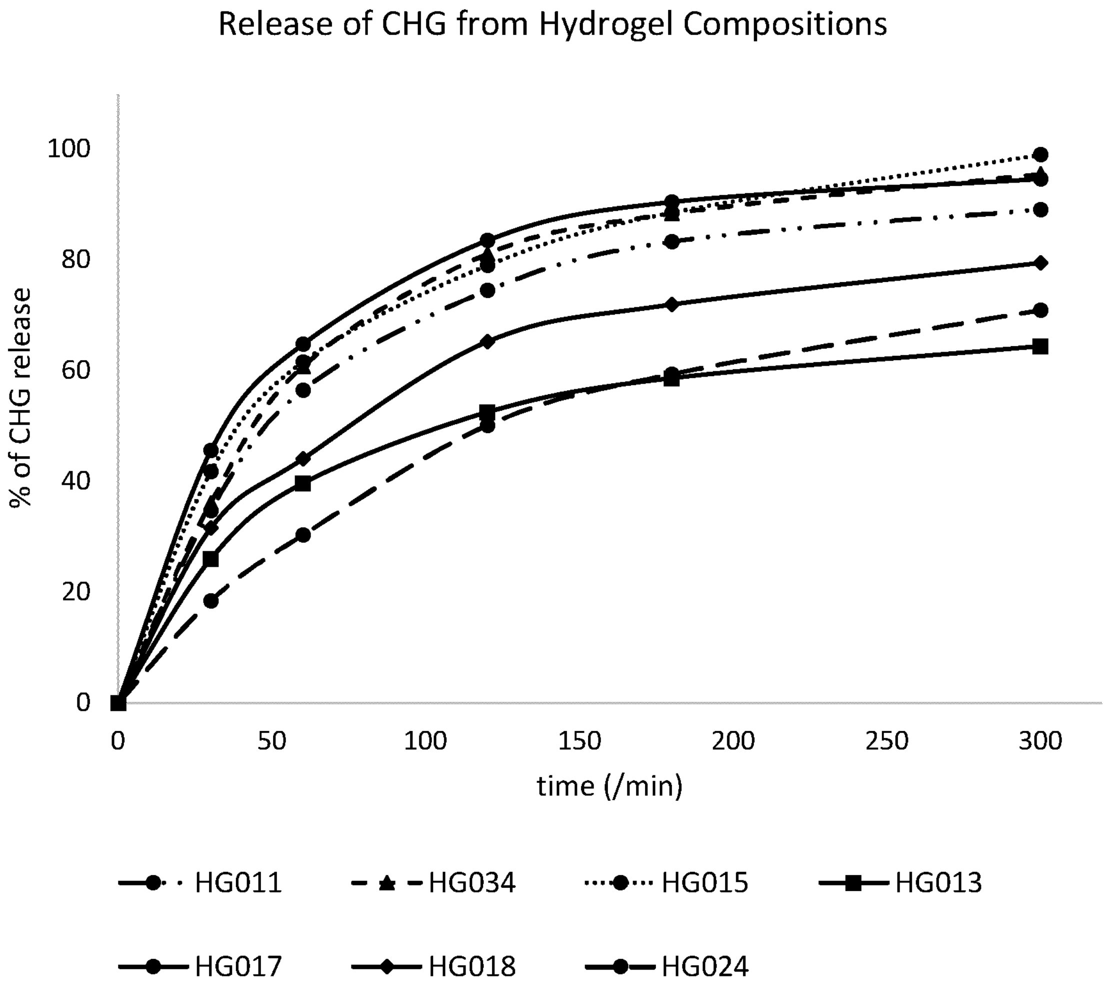
FIG. 4: Chlorhexidine gluconate release profile of hydrogel compositions containing 2% (w/w) of chlorhexidine gluconate, prepared according to table 4.

The term "functional group" is understood as generally in the state of the art, i.e., as a specific group of atoms or bonds within a molecule that is responsible for the characteristic chemical reactions of that molecule. The same functional group will undergo the same or similar chemical reaction(s) regardless of the size of the molecule it is a part of.

The term "epoxy" or "epoxide" refers to reactive compounds that are characterized by the presence of an oxirane or epoxy ring (also termed glycidyl). This is represented by a three-member ring containing an oxygen atom that is bonded with two carbon atoms already united in some other way:

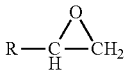

"Epoxy resin" is defined as a molecule containing more than one epoxide groups.

"Amino" group is a functional group that consists of a nitrogen atom attached by single bonds to hydrogen atoms, alkyl groups, aryl groups, or a combination of these three. Amino functional groups may be classified in primary, secondary or tertiary depending on whether one, two or the three hydrogen atoms in ammonia is replaced by an alkyl or aromatic group, respectively. Particular examples of the compositions of the invention contain polymers containing secondary or tertiary amino groups.

The term "($C_1$-$C_{10}$)-alkyl" as used herein refers to a saturated branched or linear hydrocarbon side chain with 1 to 10 carbon atoms. "($C_1$-$C_{12}$)-alkyl" may be, in particular, ($C_1$-$C_4$)-alkyl, which is for example an unsubstituted group selected from methyl, ethyl, propyl, isopropyl, butyl, isobutyl, s-butyl and t-butyl.

The term "hydrogel" is understood as a three-dimensional (3D) network of hydrophilic polymers that can swell in water and hold a large amount of water while maintaining the structure due to chemical or physical cross-linking of individual polymer chains.

The term "hydrophilic" polymer generally refers to a polymer that have affinity for water, i.e. have a tendency to mix with, dissolve in, or be wetted by water or aqueous solutions.

"Swelling agent" (sometimes also called plasticizer) is defined as a substance capable of swelling polymer.

"Modifying polymer" is defined as a polymer that, in the presence of the swelling agent, exhibits an observed reduction in the adhesiveness of the composition and maintains or increases its cohesiveness.

"Adhesion" or "adhesive" refers to a property of a substance rendering it capable of bonding other substances together, typically by surface attachment. Appropriate Adhesiveness may be determined methods well known in the state of the art, for example, by the rolling ball tack test described in the standard test method UNE-EN 1721.

The expression "% by weight" or "% wt" is understood as weight percentage of the referred ingredient with respect to the total amount of the final composition. In the present invention % wt usually refers to % w/w, in other words, x % by weight of ingredient A represents x grams of ingredient A in 100 g of the total composition. The sum of the % wt of the ingredients in the composition must be 100.

"Molar percentage" or "Mole percent" or

"Mol %" is the mole fraction for the ingredient multiplied by 100. The sum of the molar percentages for each ingredient in a composition will be equal to 100.

The first aspect of the present invention refers to an composition with improved properties when compared to prior art that comprises: a) a crosslinked hydrophilic polymer containing amino functional groups, and b) a swelling agent, wherein the crosslinked hydrophilic polymer a) is obtainable by reacting a hydrophilic polymer containing amino functional groups with a crosslinking agent, which contains at least two epoxide functional groups. In particular examples, the amino functional groups are secondary or tertiary. In particular embodiments, the hydrophilic polymer contains tertiary amino functional groups.

The composition of the invention is in the form of a hydrogel. In some embodiments, the hydrogels of the invention have a shore hardness from 20 to 80 shore units determined using a type 00 durometer as described in the standard test method ASTM D2240-15. In other embodiments the shore hardness of the hydrogels is from 35 to 65, for example from 45 to 55, as determined by the standard test method ASTM D2240-15.

In some embodiments, the composition of the invention is also transparent. In the sense of the present invention, the transparency (herein also termed as optical clarity) may be measured as the transmittance of a 2 mm thick hydrogel determined at a wavelength of 600 nm in a UV/Vis spectrophotometer. In particular embodiments, the optical clarity of the composition of the invention measured as the transmittance of a 2 mm thick hydrogel determined at a wavelength of 600 nm in a UV/Vis spectrophotometer is above 40%, for example above 50%, for example from 50 to 60%.

The composition of the invention may be colorless. Colored compounds are colored because of the absorption in the visible radiation spectrum, i.e. 380-720 nm. In particular embodiments, the UV/Vis spectrum of the composition of the invention recorded between 380 and 720 nm using a spectrophotometer does not show any absorption bands and is therefore colorless.

The composition of the invention is mostly also skin-compatible. Skin-compatibility may be determined following standard procedure ISO 10993. All these advantageous properties make the composition of the invention very appropriate for use in different application, such as wound-dressing or medical sealing.

The composition of the invention in particular embodiments is an adhesive composition. In some embodiments, the compositions have adhesiveness ranging from 1 to 50 mm (as measured by the rolling ball tack test described in the standard test method UNE-EN 1721). In particular embodiments, the adhesiveness of the composition of the invention is from 5 to 25 mm.

The composition of the invention may optionally contain a modifying polymer present in an amount sufficient to form, upon curing, a cohesive hydrogel composition. It also may contain additional compounds, such as cosmetic or pharmaceutical active ingredients (disinfectants, antibiotics, anti-inflammatories, etc) and may provide controlled release of said compounds to the skin. The composition of the invention can also contain other additives to control the mechanical and optical properties, such as adhesiveness, cohesiveness, colour and transparency, of the resulting hydrogel.

Crosslinked Hydrophilic Polymer Containing Amino Functional Groups

The crosslinked hydrophilic polymer is obtainable by the reaction of a hydrophilic polymer containing amino functional groups with a crosslinking agent, which contains at least two epoxide functional groups. For example, the hydrophilic polymer contains secondary or tertiary amino functional groups. The crosslinking reaction is therefore a chemical crosslinking, and does not require irradiation. This chemical crosslinking may take place by mixing the hydrophilic polymer containing amino functional groups with the crosslinking agent, which contains at least two epoxide functional groups in the presence of a volatile solvent at a temperature from 40 to 100° C. during a time from 1 to 24 hours. The crosslinking reaction may take place before mixing with the swelling agent. Alternatively, the crosslinking may take place when mixing with the swelling agent at the conditions for forming the composition of the invention. The latter case is convenient, since the crosslinking and the formation of the composition takes place simultaneously in only one step.

Hydrophilic Polymer Containing Amino Functional Groups

In most embodiments, the hydrophilic polymer containing amino functional groups is a random co-polymer of formula I Formula I

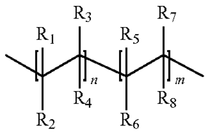

wherein:

n and m are independently selected from an integer from 100 to 50,000.

$R_1$, $R_2$, $R_4$, $R_5$, $R_6$ and $R_8$ are each independently selected from —H, —OH and $C_1$-$C_6$ alkyl optionally substituted by at least one hydroxyl group;

$R_3$ is selected from:

(i) —OH, (ii) N-lactam, (iii) —$COOR_9$, wherein $R_9$ is selected from —H, $C_1$-$C_6$ alkyl optionally substituted by at least one group selected from a hydroxyl group and —($CH_2$—$CH_2$—O)$_p$—H wherein p is an integer from 1 to 10, (iv) —$CONR_{10}R_{11}$, wherein $R_{10}$ and $R_{11}$ are independently selected from —H, $C_1$-$C_6$ alkyl optionally substituted by at least one group selected from a hydroxyl group and —(CH2-CH2-O)$_p$—H wherein p is an integer from 1 to 10, (v) —$NHCOR_{12}$, wherein $R_{12}$ is selected from $C_1$-$C_6$ alkyl optionally substituted by at least one group selected from a hydroxyl group and —(CH2-CH2-O)$_p$—H wherein p is an integer from 1 to 10, and (vi) —($CH_2$—$CH_2$—O)$_p$—H wherein p=1-10; and R7 is selected from:

(i) —$COOR_{13}$, wherein $R_{13}$ is $C_1$-$C_6$ alkyl substituted by at least one amino functional group, (ii) —$CONR_{14}R_{15}$, wherein $R_{14}$ is $C_1$-$C_6$ alkyl substituted by at least one amino functional group and $R_{15}$ is selected from —H, $C_1$-$C_6$ alkyl optionally substituted by at least one group selected from a hydroxyl group, an amino functional group and —($CH_2$—$CH_2$—O)$_p$—H wherein p=1-10, and (iii) —$NHCOR_{14}$, wherein $R_{14}$ is selected from $C_1$-$C_6$ alkyl optionally substituted by at least one group selected from a hydroxyl group and —(CH2-CH2-O)$_p$—H wherein p is an integer from 1 to 10.

"Random" copolymers are those in which the different monomer residues are located randomly in the polymer molecule. In the sense of the present invention, the hydrophilic polymer that contains amino functional group, particularly secondary or tertiary amino functional groups, may be a random copolymer with formula I as defined above, wherein the structure delimited by brackets define monomers, which are randomly distributed within the polymer n and m times, wherein n and m are independently selected from an integer from 100 to 50,000. In some embodiments, n and m are independently selected from an integer from 1000 to 20,000 The amino groups are, in particular embodiments, tertiary amino functional groups.

In some particular embodiments, $R_1$, $R_2$, $R_5$ and $R_6$ are —H.

In some particular embodiments, $R_4$ and $R_8$ are —H or —$CH_3$.

In some particular embodiments, $R_3$ is selected from: (i) —OH, (ii) N-lactam, (iii) —$COOR_9$, wherein $R_9$ is selected from —H, —$CH_3$, $C_2$-$C_4$ optionally substituted by at least one group selected from a hydroxyl group and —(CH2-CH2-O)$_p$—H wherein p is an integer from 1 to 10, and (iv) —$CONR_{10}R_{11}$, wherein $R_{10}$ and $R_{11}$ are —H.

In some particular embodiments $R_3$ is selected from: (i) —OH, (ii) N-pyrrolidone, (iii) —$COOR_9$, wherein $R_9$ is selected from —$CH_2$—$CH_2OH$, —($CH_2$—$CH_2$—O)$_p$—H wherein p=1-5, and (iv) —$CONR_{10}R_{11}$, wherein $R_{10}$ and $R_{11}$ are —H.

In some embodiments $R_7$ is selected from —COO—$CH_2$—$CH_2$—$NH_2$, —COO—$CH_2$—$CH_2$—N($CH_3$)$_3$ and —CONH—$CH_2$—$CH_2$—N($CH_3$)$_3$.

In some particular embodiments, $R_1$, $R_2$, $R_5$ and $R_6$ are —H; $R_4$ and $R_8$ are —H or —$CH_3$; $R_3$ is selected from: (i) —OH, (ii) N-pyrrolidone, (iii) —$COOR_9$, wherein $R_9$ is selected from —$CH_2$—$CH_2OH$, —($CH_2$—$CH_2$—O)$_p$—H wherein p=1-5, and (iv) —$CONR_{10}R_{11}$, wherein $R_{10}$ and $R_{11}$ are —H; and $R_7$ is selected from —COO—$CH_2$—$CH_2$—$NH_2$, —COO—$CH_2$—$CH_2$—N($CH_3$)$_3$ and —CONH—$CH_2$—$CH_2$—N($CH_3$)$_3$.

In particular embodiments, the hydrophilic co-polymer polymer containing secondary or tertiary amino functional groups is selected from poly(2-hydroxyethyl methacrylate-co-2-aminoethyl methacrylate), poly(acrylamide-co-2-aminoethyl methacrylate), poly(2-hydroxyethyl methacrylate-co-2-dimethylaminoethyl methacrylate), poly(1-vinylpyrrolidone-co-2-dimethylaminoethyl methacrylate), poly(acrylamide-co-2-dimethylaminoethyl methacrylate), poly(vinyl alcohol-co-n-[3-(dimethylamino)propyl]methacrylamide and poly(acrylamide-co-3-dimethylaminopropyl methacrylamide). In particular examples the hydrophilic co-polymer polymer containing secondary or tertiary amino functional groups is poly(1-vinylpyrrolidone-co-2-dimethylaminoethyl methacrylate).

The invention also contemplates providing a hydrophilic polymer containing amino functional groups (particularly secondary or tertiary), which is not necessarily a co-polymer as the one in formula I. Other polymers are also contemplated for use in the present invention. Generally speaking, the hydrophilic polymers appropriate for the present invention are water-soluble or alcohol-soluble hydrophilic polymers. The hydrophilic polymer containing amino functional groups may be obtained by co-polymerization of hydrophilic monomers and amine-containing monomers as in formula I. It is also contemplated, however, that the amine functionalities, particularly secondary or tertiary, more particularly tertiary amine functionalities, are introduced in a hydrophilic polymer by chemical modification of the polymer chains. Non-limiting examples of hydrophilic polymers include: polyglycerol, poly(amidoamine) poly(aminoester), derivatives of polysaccharides (such as cellulose, dextran, chitosan, guar gum, xantan gum or hyaluronic acid among others), polyacrylic acid, polymethacrylic acid, poly(meth) acrylamides (such as polyacrylamide, polymethacrylamide, poly(N,N-diethylacrylamide), poly(N,N-dimethylmethacrylamide), poly(N-ethylmethacrylamide), poly(N-isopropylacrylamide), poly(N-(hydroxyethyl)acrylamide), poly(N-(hydroxyethyl) methacrylamide), poly(N-(hydroxypropyl) acrylamide), poly(N-(hydroxypropyl) methacrylamide), poly(meth)acrylates (such as poly(2-hydroxyethyl acrylate), poly(2-hydroxyethyl methacrylate), poly(hydroxypropyl acrylate), poly(hydroxypropyl methacrylate), poly(glycerol monomethacrylate), poly(glycerol monoacrylate), polyethyleneglycol acrylate, polyethyleneglycol methacrylate), poly(N-vinyl lactams) (such as poly(N-vinyl pyrrolidone), poly(N-vinyl valerolactam), poly(N-vinyl caprolactam)), poly(vinyl alcohol), poly(N-vinyl acetamide), polyethylene glycol and others. Alternatively, the poly(N-vinyl lactam) copolymer may be partially crosslinked, either in solution during copolymerization or by irradiation after copolymerization.

Examples of chemical modification of polymer chains to introduce amine functionalities are available in the literature, e.g.: modification of polyvinyl alcohol with N-alkyl-substituted groups (Polym. Chem., 2017, 8, 5769-5779), modification of poly(2-hydroethyl methacrylate) with 2-chloro-N,N-diethylethylamine hydrochloride (J. Sep. Science, 2005, 28, 1855-1875), esterification of polyacrylic acid with N-alkyl-substituted alkanolamines (EP1061089B1), reductive amination of oxidized dextran with amines (J. Control Release, 2008, 125, 246-251). Alternatively, suitable polymers containing amine functionalities may be obtained by derivatization via chemical means known by those skilled in the art.

The molar percentage of the monomers that contain an amino functional group in the hydrophilic polymer is generally from 1% to 60%. In some embodiments, the molar percentage of the monomers that contain amino functional group in the hydrophilic polymer is generally from 1% to 50%, or 2% to 40%, or from 3% to 35%, or from 4% to 30%, or from 5% to 25%, for example 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%.

In most examples, the amino functional group is secondary or tertiary, in particular, tertiary functional group.

Any of the hydrophilic polymers or co-polymers mentioned above may be obtained by known polymerization methods. Most of them are also commercially available.

For producing the polymers, appropriate amounts of monomer are subjected, for example, to step-growth or chain-growth polymerization. Appropriate monomers for producing the hydrophilic polymers useful for the invention are those which, upon polymerization, render a water-soluble or alcohol-soluble hydrophilic polymer. The amine functional groups, particularly secondary, more particularly, tertiary amine functional groups, may be introduced in the hydrophilic copolymer either by chemical modification of the polymer chains or by co-polymerization of hydrophilic monomers and amine-containing monomers. Non-limiting examples of appropriate monomers include: glycerol, amidoamine aminoester, derivatives of saccharides (such as glucose, fructose or hyaluronic acid among others), acrylic acid, methacrylic acid, (meth)acrylamides (such as acrylamide, methacrylamide, N,N-diethylacrylamide, N,N-dimethylmethacrylamide, N-ethylmethacrylamide, N-isopropylacrylamide, N-(hydroxyethyl)acrylamide, N-(hydroxyethyl) methacrylamide, N-(hydroxypropyl)acrylamide, N-(hydroxypropyl) methacrylamide, (meth)acrylates (such as 2-hydroxyethyl acrylate, 2-hydroxyethyl methacrylate, hydroxypropyl acrylate, hydroxypropyl methacrylate, glycerol monomethacrylate, glycerol monoacrylate, ethyleneglycol acrylate, ethyleneglycol methacrylate, N-vinyl lactams (such as N-vinyl pyrrolidone, N-vinyl valerolactam, N-vinyl caprolactam), vinyl alcohol, N-vinyl acetamide, ethylene glycol and others.

In most embodiments, the hydrophilic polymer of the invention comprises a monomer of formula II:

Formula II

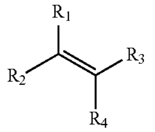

wherein $R_1$, $R_2$, $R_3$ and $R_4$ are as described above for formula I.

In most embodiments, a hydrophilic vinylic monomer such as those mentioned above is copolymerized together with a secondary or tertiary amine-containing monomer in a sufficient amount to provide sufficient amine functionalities in the polymer chain suitable for crosslinking with a crosslinking agent, which contains at least two epoxide functional groups (also herein referred to as multifunctional epoxides) and allow the formation of a cohesive hydrogel. In particular embodiments, the amine-containing vinyl monomer contains a tertiary amino group. Non-limiting examples of tertiary amine-containing vinyl monomers include: 2-(dimethylamino)ethyl (meth)acrylate, 2-(diethylamino)ethyl (meth)acrylate, 2-(diisopropylamino)ethyl (meth)acrylate), 2-aminoethyl (meth)acrylate, 2-(tert-butylamino)ethyl (meth)acrylate, 3-(dimethylamino)propyl (meth)acrylate), 2-(dimethylamino)ethyl (meth)acrylamide, N-[3-(dimethylamino)propyl] (meth)acrylamide, N-(3-aminopropyl) (meth)acrylamide), 2-aminoethyl (meth)acrylamide, and mixtures of any of the foregoing monomers. In a most particular embodiment, the amine-containing vinyl monomer is 2-(dimethylamino)ethyl methacrylate. Alternatively, suitable polymers containing amine functionalities may also be obtained by derivatization of hydrophilic polymers to render amine-containing hydrophilic polymers via chemical means known by those skilled in the art.

The hydrophilic polymer of the invention
thus comprises in some embodiments a monomer of formula III:

Formula III

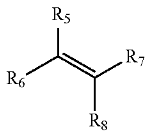

wherein $R_5$, $R_6$, $R_7$ and $R_8$ are as described above for formula I.

In most embodiments, the molar percentage of the monomers in the hydrophilic polymer that contains an amino functional group may be from 1% to 60%. In particular embodiments, the molar percentage of the monomers in the hydrophilic polymer that contains an amino functional group may be from 1% to 50%, or 2% to 40%, or from 3% to 35%, or from 4% to 30%, or from 5% to 25%, for example 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%. The amino functional group may be secondary or tertiary, more particularly, tertiary functional group.

The molecular weight of the hydrophilic polymer containing amine functional groups may be from 10,000 to 10,000,000. In some embodiments, said molecular weight is from 100,000 to 5,000,000, particularly from 200,000 to 2,000,000.

Crosslinking Agent

The crosslinking agent of the present invention comprises a multifunctional epoxide compound to provide sufficient reactive sites suitable for crosslinking of at least 2 polyfunctional copolymer chains and allow the formation of a crosslinked polymeric network. In most embodiments, the number of epoxide functional groups is equal or greater than 2 per epoxide-containing compound. In particular embodiments, the polyfunctional epoxide crosslinkers are low-molecular weight compounds and compatible with the reaction matrix in order to maximize crosslinking uniformity and density throughout the entire polymeric network and ensure excellent optical clarity.

In most embodiments, the crosslinking agent is selected from $C_4$-$C_{12}$ alkyl diepoxides, di-glycidyl ethers, tri-glycidyl ethers, poly-glycidyl ethers and tris(2,3-epoxypropyl) isocyanurate.

Non-limiting examples of suitable crosslinkers for the present invention include: butadiene diepoxide, ethyleneglycol diglycidyl ether, glycerol diglycidyl ether, butanediol diglycidyl ether, diethyleneglycol diglycidyl ether, hexanediol diglycidyl ether, resorcinol diglycidyl ether, neopentyl glycol diglycidyl ether, glycerol triglycidyl ether, triphenylolmethane triglycidyl ether, glycerol polyglycidyl ether, tris(2,3-epoxypropyl) isocyanurate, trimethylolpropane polyglycidyl ether, pentaerythritol polyglycidyl ether, polyethylene glycol diglycidyl ether, polypropylene glycol diglycidyl ether, sorbitol polyglycidyl ether, polyglycerol polyglycidyl ether, 4-arm PEG-epoxide, 8-arm PEG-epoxide, methoxy-peg glycidyl ether, ethoxylated polyalcohols polyglycidyl ether, and numerous other compounds containing two or more epoxy groups including epoxy resins commonly used in commercial epoxy formulations.

In some embodiments, the crosslinking agent is selected from the group consisting of ($C_2$-$C_{12}$)-alkylenglycol, di-, tri-, or poly-glycidyl ether and (($C_2$-$C_{12}$)-alkylenglycol), di-, tri-, or poly-glycidyl ether, where n is an integer from 2 to 80. In some particular embodiments the crosslinking agent is selected from ethyleneglycol diglycidyl ether, glycerol diglycidyl ether, butanediol diglycidyl ether, diethylene glycol diglycidyl ether, hexanediol diglycidyl ether, neopentyl glycol diglycidyl ether, glycerol triglycidyl ether, glycerol polyglycidyl ether, trimethololpropane polyglycidyl ether, pentaerythritol polyglycidyl ether, polyethylene glycol diglycidyl ether, polypropylene glycol diglycidyl ether, sorbitol polyglycidyl ether, polyglycerol polyglycidyl ether, and combination thereof. For example the crosslinking agent may be selected from glycerol diglycidyl ether, poly(ethylene glycol) diglycidyl ether, diethylene glycol diglycidyl ether, ethylene glycol diglycidyl ether, 1,4-butanediol diglycidyl ether, pentaerythritol polyglycidyl ether and sorbitol diglycidyl ether. In a particular example the crosslinking agent is polyethylene glycol diglycidyl ether, particularly, having average Mn=500.

Swelling Agent

The composition of the invention comprises a swelling agent to control the viscoelastic and the mechanical properties of the resulting crosslinked polymeric network. The swelling agent can be any compatible agent that is capable of swelling the polymeric network and the modifying polymer,
particularly rendering a highly transparent hydrogel. The swelling agent may be volatile, e.g. to control the viscosity of the mixture of components in the fabrication of hydrogels, or non-volatile, e.g. to control the viscoelastic properties of the resulting hydrogel. In this invention, "non-volatile" swelling agent means that less than a 10% of the swelling agent is evaporated throughout the processing steps of the final hydrogel. "Volatile" swelling agent in the present invention means that more than a 10% of the swelling agent is evaporated throughout the processing steps of the final hydrogel. In some embodiments, a mixture of any ratio of volatile and non-volatile swelling agents can be used.

Swelling agents comprised in the composition of the invention are generally selected from the group consisting of water, monohydric alcohols, polyhydric alcohols, ethoxylated polyhydric alcohols, methyl ethers of ethoxylated polyhydric alcohols, and combinations thereof. Non-limiting examples of volatile and non-volatile swelling agents include: water, ethanol, n-propanol, isopropanol, ethylene glycol, propylene glycol, 1,4-butanediol, polyethylene glycol, glycerine, glycerol, diglycerol, triglycerol, polyglycerol, and derivatives thereof, and other polyol plasticizer agents suitable for biomedical applications. In some embodiments, the non-volatile swelling agent is chosen from glycerol, diglycerol, triglycerol and polyethylene glycerol with number average molecular weight (Mn) between 200 and 800. In some embodiments, the volatile swelling agent is chosen from water, ethanol and isopropanol. In particular examples, the volatile swelling agent is chosen from glycerol, diglycerol, triglycerol and tetraglycerol.

The swelling agent is typically a liquid, but in some embodiments, liquid swelling agents may be partially replaced with solid swelling agents, such as erythritol, sorbitol, urea or polyethylene glycol with Mn>800 among others, as long as the resulting mixture remains a liquid at the processing conditions. Non-limiting examples of other solid swelling agents include: glycosaminoglycans (e.g. hyaluronic acid, or keratan sulphate), hydrolysed proteins (e.g. hydrolysed collagen, hydrolysed elastin or hydrolysed silk), monosaccharides (e.g. glucose, fructose or gluconic acid), disaccharides (e.g. sucrose or maltitol), polysaccharides (e.g. polydextrose or polyglucuronic acid), urea and derivatives (e.g. hydroxyethyl urea or allantoin), aminoacids (e.g. glutamic acid or glycine) and hydroxyacids (e.g. lactic acid or lactobionic acid), and other polyol swelling agents suitable for biomedical applications.

Modifying Polymer

The composition of the present invention may include one or more modifying polymers to adjust the adhesiveness, cohesiveness and viscoelastic properties of the resulting composition. The modifying polymers may also be used to improve the appearance and the optical properties of the resulting hydrogel. The modifying polymers can be solubilized or swollen and uniformly solubilized or suspended in the swelling agent of choice for the particular composition.

Examples of suitable modifying polymers may include the following polymers or their derivatives: polysaccharides, poly(meth)acrylates, poly(meth)acrylamides, poly(meth) acrylic acids, polyvinyl alcohols, polyvinylpyrrolidones, polyethylene glycols, polypropylene glycols, celluloses, polysiloxanes, or combinations thereof. Non-limiting examples of modifying polymers include: guar gum, karaya gum, xanthan gum, hydroxypropyl guar, hydroxyethyl cellulose, hydroxypropyl cellulose, quaternary ammonium salt of hydroxyethyl cellulose, polyacrylamide, polyvinyl alcohol, polyvinylpyrrolidone, polyether-modified polysiloxane, poloxamer, and other modifying agents suitable for biomedical applications. In particular embodiments, the modifying polymer is selected from the group consisting of guar gum, karaya gum, xanthan gum, hydroxypropyl guar, hydroxyethyl cellulose, hydroxypropyl cellulose, quaternary ammonium salt of hydroxyethyl cellulose, polyacrylamide, polyvinyl alcohol, polyvinylpyrrolidone, polyether-modified polysiloxane, poloxamer, and combinations thereof.

Other Ingredients

There are numerous therapeutic, biological and cosmetic active substances, which may be included in the composition of the present invention, depending on the intended use of the product. The composition of the present invention can include such an active substance that can be delivered to the skin, in or around the hydrogel.

In some embodiments, the composition of the present invention can include an active pharmaceutical ingredient. For example, the active pharmaceutical ingredient is an antimicrobial agent that can be delivered to the skin to reduce the likeliness of infection of the skin, a wound or an insertion point of a percutaneous device. Non-limiting examples of antimicrobial agents include: antibiotics (e.g. bacitracin, erythromycin or neomycin) chlorhexidine and its salts (e.g. chlorhexidine gluconate), sulphonamides (e.g. sulfacetamide or sodium fusidate), peroxides (e.g. benzoyl peroxide), triclosan, polyhxamethylene biguanidine chloride,
silver and its salts, iodine and its derivatives (e.g. povidone-iodine), fatty acid monoesters, essential oils, and other antimicrobial agents suitable for therapeutic applications.

In other embodiments, the composition of the present invention may include a healing agent to assist skin regeneration and/or reduce scar formation of wounds, burns, ulcers and lacerations, punctures, biopsy wounds, blisters, tattoos, and other skin injuries. Non-limiting examples of healing agents include: collagen and its hydrolysates, hyaluronic acid, growth factors (e.g. endothelial growth factor or fibroblast growth factor), essential oils, polysaccharides (e.g. chitin and its derivatives), and other healing agents suitable for therapeutic applications.

In another particular embodiment, the composition of the present invention includes a therapeutic agent to topically treat mild to moderate conditions of skin diseases or disorders. Typical skin diseases and disorders and their corresponding therapeutic agents that can be included in the compositions of the present invention include: psoriasis, acne, dermatitis, eczema, impetigo, hives, blister, keratosis, rosacea, basal cell carcinoma, warts, cold-sore, and any other skin disorder o disease that may be topically treated or ameliorated. Non-limiting examples of skin conditions and corresponding therapeutic agents include: psoriasis (e.g. corticosteroids, vitamin D analogues, anthralin, retinoids, calcineurin inhibitors, salicylic acid, coal tar, urea and/or moisturizers), acne (e.g. retinoids, antibiotics, salicylic acid, azelaic acid, dapsone and/or peroxides), eczema (e.g. corticosteroids, calcineurin inhibitors, antibiotics and/or moisturizers), impetigo (e.g. antibiotics), rosacea (e.g. antibiotics, azelaic acid and/or dapsone), hives (e.g. antihistamines), actinic keratosis (e.g. fluorouracil, imiquimod, diclofenac, ingenol mebutate and/or trichloroacetic acid), basal cell carcinoma (e.g. fluorouracil and/or imiquimod), warts (e.g. salicylic acid and/or trichloroacetic acid), cold-sore (e.g. acyclovir, famciclovir and/or valacyclovir), and other therapeutic agents suitable for treating skin diseases or disorders.

The composition of the invention may thus contain an active pharmaceutical ingredient selected from the group consisting of antimicrobials, analgesics, anti-inflammatory agents, clotting agents, growth factors, anti-pruritic agents. In particular embodiments, the composition of the invention contains an antimicrobial, for example chlorhexidine gluconate.

In another embodiment, the composition of
the present invention includes a cosmetic active ingredient to enhance, cleanse, beautify or alter the appearance of the skin. Depending on the use of the composition of the present invention, various cosmetic ingredients can be included in the composition. Non-limiting examples of different types of cosmetic agents include: antiseborrhoeic, astringent, bleaching, peeling, cleansing, emollient, hydrotropic, regenerative, refatting, smoothing, soothing, antioxidant, humectant, keratolytic, moisturizing, skin protecting, antiaging, oxidizing, reducing, and other cosmetic agents suitable for cosmetic or cosmeceutic applications and known to those skilled in the art.

Other compatible ingredients can be added to the composition, such as compounds to adjust the pH of the composition. In addition, when the composition of the invention includes pharmaceutical, biological, or cosmetic agents, excipients, preservatives, emulsifiers or skin penetration enhancers can be added to suit the topical or transdermal delivery of such agents. When the composition of the invention comprises excipients and carriers, these are particularly for topical application, i.e. topically acceptable excipients and carriers.

Composition

In some embodiments, the composition of the invention may contain: a) from 5% to 50% by weight of cross-linked hydrophilic polymer containing amino functional groups, and b) at least 40% by weight of swelling agent. Percentages by weight are referred to the total weight of the composition. Optionally, the composition may comprise at least one further compound selected from c) or d), wherein c) is no more than 10% by weight of modifying polymer compatible with the swelling agent and d) is no more than 25% by weight of active pharmaceutical or cosmetic ingredient.

In other embodiments, the composition of the invention may contain: a) from 5% to 50% by weight of cross-linked hydrophilic polymer containing amino functional groups, b) from 40% to 80% by weight of swelling agent, and optionally at least one further compound selected from c) or d), wherein c) is from 0.5% to 10% by weight of modifying polymer compatible with the swelling agent and d) is from 0.5% to 25% by weight of active pharmaceutical or cosmetic ingredient.

In other embodiments, the composition comprises: a) from 20% to 40% by weight of cross-linked hydrophilic polymer containing amino functional groups, b) from 50% to 70% by weight of swelling agent, and optionally at least one further compound selected from c) or d), wherein c) is from 1% to 10% by weight of modifying polymer compatible with the swelling agent and d) is from 0.5% to 15% by weight of active pharmaceutical or cosmetic ingredient.

In other embodiments, the composition comprises: a) from 20% to 35% by weight of cross-linked hydrophilic polymer containing amino functional groups, b) from 55% to 65% by weight of swelling agent and d) from 1% to 10% by weight of active pharmaceutical or cosmetic ingredient.

In other embodiments, the composition comprises: a) from 20% to 35% by weight of cross-linked hydrophilic polymer containing amino functional groups, b) from 55% to 65% by weight of swelling agent, from 2% to 8% by weight of modifying polymer compatible with the swelling agent and d) from 1% to 10% by weight of active pharmaceutical or cosmetic ingredient.

In particular embodiments, the composition of the invention is a pharmaceutical composition. In other particular embodiments, the composition of the invention is a cosmetic composition. In other particular embodiments, the composition of the invention is a medical device. In other particular embodiments, the composition of the invention is a sanitary product.

Method for Preparing the Compositions

A second aspect of the invention provides method for obtaining a composition as defined above which comprises:

(i) mixing in the presence of a volatile solvent: a hydrophilic polymer containing amino functional groups, a swelling agent, a crosslinking agent which contains at least two epoxide functional groups, (ii) subjecting the mixture to a temperature from 40 to 100° C. during 1 to 24 hours, and optionally (iii) placing in an aqueous solution for swelling.

The amino functional groups are usually secondary or tertiary amino functional groups, particularly tertiary.

Step (i) may optionally include mixing at least one further ingredient selected from a modifying polymer compatible with the swelling agent and other active ingredients (such as active pharmaceutical ingredients, cosmetic ingredients, excipients, etc). The components mixed in step (i) have been extensively defined above and also apply here.

Examples of volatile solvents include water, ethanol and isopropanol, or mixtures thereof. The resulting mixture is vigorously mixed and then casted onto an appropriate surface, such as a release liner or a non-adherent mould. The mixture is allowed to cure, and the volatile solvent is evaporated by heating to obtain a cohesive, and optionally adhesive, composition. The resulting hydrogel composition can be cut into individual units using dies or other appropriate tools.

The stoichiometry of the reaction may depend on the use of the final product. For example, in most embodiments, the mix of step (i) in the method of the invention contains: from 5% to 35% by weight of hydrophilic polymer containing amino functional groups, no more than 10% crosslinking agent, at least 15% by weight of swelling agent and solvent up to 100%. In some embodiments, step (i) also comprises mixing no more than 10% by weight of modifying polymer compatible with the swelling agent and/or no more than 25% by weight of active pharmaceutical or cosmetic ingredient.

In some embodiments, step (i) comprises mixing from 10% to 25% by weight of hydrophilic polymer containing amino functional groups, from 0.1% to 10% by weight of crosslinking agent, from 15% to 35% by weight of swelling agent, optionally at least one further compound selected from 0.1% to 10% by weight of modifying polymer compatible with the swelling agent and from 0.5% to 15% by weight of active pharmaceutical or cosmetic ingredient and solvent up to 100.

In other embodiments, step (i) comprises mixing from 10% to 18% by weight of hydrophilic polymer containing amino functional groups, from 1 to 5% by weight of crosslinking agent, from 20% to 30% by weight of swelling agent, optionally at least one further compound selected from 0.5% to 5% by weight of modifying polymer compatible with the swelling agent and from 1% to 10% by weight of active pharmaceutical or cosmetic ingredient, and solvent up to 100.

In other embodiments, step (i) comprises mixing from 10% to 15% by weight of hydrophilic polymer containing amino functional groups, from 1 to 4% by weight of crosslinking agent, from 20% to 30% by weight of swelling agent, optionally from 0.5% to 5% by weight of modifying polymer compatible with the swelling agent, from 1% to 5% by weight of active pharmaceutical or cosmetic ingredient, and solvent up to 100.

As already mentioned, the crosslinked polymer network of the hydrogel composition of the present invention is obtained by reacting a mixture of polyfunctional amine and polyfunctional epoxide compounds. In most embodiments, the composition of polyfunctional amine and polyfunctional epoxide compounds is adjusted so that the mixture will produce a hydrogel under the conditions of reaction. The mechanical properties of the resulting crosslinked polymer network can be controlled by the extent of crosslinking and the nature of the crosslinking agent. In a particular embodiment, the hydrophilic polymer containing amino functional groups is in excess in terms of the amino functionality of the reagent to allow full reaction of the epoxide functional groups of the crosslinking agent.

Figure 5:
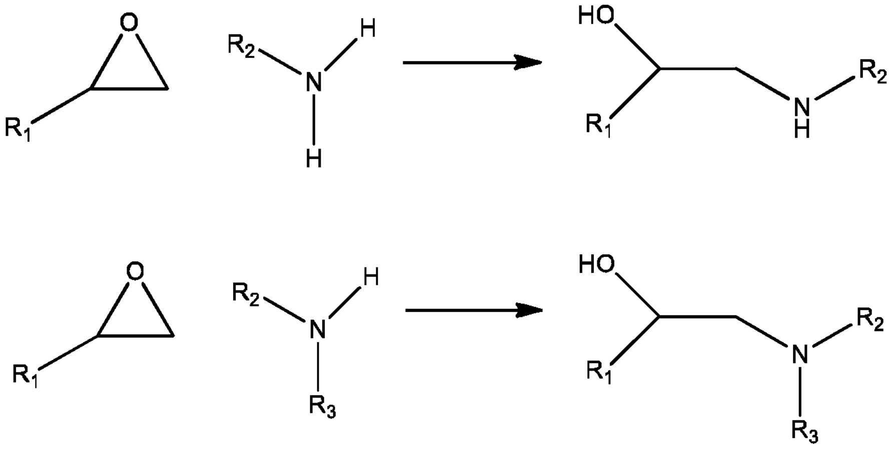
FIG. 5: Reaction of epoxides and primary and secondary amines. R is H, alkyl or aryl.
Figure 6:
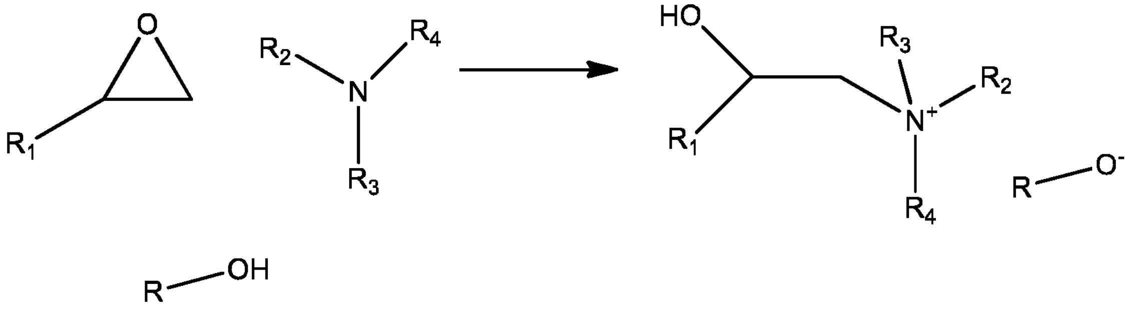
FIG. 6: Reaction of epoxides and tertiary amines. R is H, alkyl or aryl. R is H, alkyl or aryl.
Figure 7:
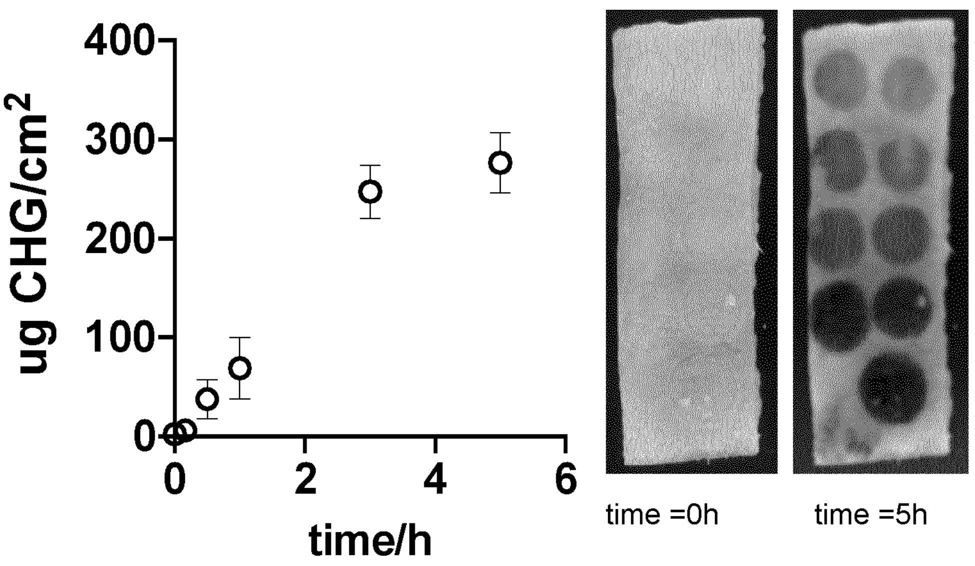
FIG. 7: Release of chlorhexidine gluconate (CHG) from hydrogel composition to porcine skin after different contact times (0 to 5 hours). The accumulative release is expressed as amount of CHG per area of skin against contact time.

In general terms, epoxides and primary and secondary amines react as described in the equation shown in FIG. 5. In general terms, epoxides and tertiary amines react as described in the equation shown in FIG. 6.

In the case of tertiary amines, the reaction product is a quaternary ammonium ion. This reaction requires one mole of water and the counterion formed spontaneously as a byproduct of the reaction is a hydroxide anion. Alternatively, the reaction may proceed with one mole of alcohols (or other proton donors) according to the mechanism described in the previous figure to yield quaternary ammonium alcoholate as the crosslinking point.

In a particular embodiment, the hydrophilic polymer containing amino functional groups is in excess in terms of the amino functionality of the reagent to allow full reaction of the epoxide functional groups of the crosslinking agent. Using this composition allows formation of a crosslinked polymer network. The condensation polymer network formed with this composition contains a significant number of crosslinking points, forming quaternary ammonium sites at each reaction site, that allows the formation of a hydrogel capable of maintaining its structure without dissolving.

In some embodiments, step (ii) of the method of the invention comprises a temperature form 40 and 100° C. ° C. and a time from 1 to 24 hours. In some embodiments, the temperature is from 45 to 55° C. and the time is from 12 to 24 hours.

A third aspect of the invention contemplates a composition which is obtainable by the method described above. Said composition is such as defined in the first aspect of the invention and embodiments thereof and has the same properties as described thereof. Thus, all embodiments described for the composition of the first aspect of the invention also apply to the composition obtainable by the method described in the second aspect of the invention.

The invention also provides a composition comprising the mixture of step (i) of the method of the invention, that is: a hydrophilic polymer containing amino functional groups, a swelling agent, a crosslinking agent, which contains at least two epoxide functional groups, optionally at least one further ingredient selected from a modifying polymer compatible with the swelling agent and other active ingredients (such as active pharmaceutical ingredients, cosmetic ingredients, excipients, etc), and a volatile solvent. All these components have been defined above. The amounts of the components in the mixture are as described above.

Applications

The composition of the invention may be used for several medical applications.

In one embodiment, the composition disclosed herein may be used to secure and protect vascular lines that have been inserted into a human patient. The composition of the invention provides a hydrogel system possessing desired cohesiveness and, optionally, with sufficient adhesiveness to human skin. The composition of the invention may provide sufficient adhesiveness to provide attachment of the catheter line to the skin to inhibit catheter movement and minimize any possible vascular injury. It may also possess sufficient cohesiveness to withstand catheter attachment, while leaves no significant residue on the skin when removed. In addition, the mechanical properties of the composition of the invention may be adjusted to provide a cushion effect and reduce excessive pistoning of the catheter or insertion device and limit tissue damage. Also, when placed correctly, the composition of the invention possesses barrier properties and protects the underlying vascular access point from dirt and pathogens.

In another embodiment, the composition of the invention may be used for protecting wounds, burns or any skin condition that requires the protection of compromised skin to maintain the wettability and moist in the wound, providing better wound management and healing outcome. When placed correctly, the composition of the invention possesses barrier properties and protects the underlying skin from dirt and pathogens, while its enhanced optical clarity allows continuous visualization of the underlying skin. In addition, the composition of the invention may provide absorption properties allowing the control wound exudates.

In another embodiment, the composition of the invention is also useful as a reservoir for the delivery of therapeutic agents onto or through the skin. The compositions may contain additives, excipients or penetration enhancers to control the topical or transdermal delivery of pharmaceutical and/or active ingredients. Pharmaceutically acceptable additives and excipients can also be included in the formulation of the composition of the invention to increase the solubility of the active principle in the hydrogel matrix, to adjust and/or buffer the pH, control the ionic strength, adjust the color and transparency, and/or alter the tackiness.

The compositions of the invention may be used in the manufacture of skin-contact medical articles for any of the above applications. The invention also contemplates medical articles that comprise the compositions of the invention. Said skin-contact medical articles may be wound-dressings, securement dressings, sealants, plasters, patches and the like.

When the composition comprises pharmaceutical active ingredients, the composition of the invention as described above may be for use as a medicament. This may also be formulated as a composition as described above for the preparation of a medicament. The invention also contemplates a method of treating or preventing a medical condition comprising administering the composition as defined above, together with pharmaceutically acceptable excipients or carriers, in a subject in need thereof, including a human. The medicament may be for treating or preventing a medical condition, which is a skin condition, for example selected from wounds, ulcers, burns, psoriasis, acne, dermatitis, eczema, impetigo, hives, blister, keratosis, rosacea, basal cell carcinoma, warts and cold-sore. Thus, the composition as described above may be for use in the prevention or treatment of a sin disorder, for example one selected from wounds, ulcers, burns, psoriasis, acne, dermatitis, eczema, impetigo, hives, blister, keratosis, rosacea, basal cell carcinoma, warts and cold-sore. This may be reformulated as a composition as described above for use in the preparation of a medicant for the prevention or treatment of a sin disorder, for example one selected from wounds, ulcers, burns, psoriasis, acne, dermatitis, eczema, impetigo, hives, blister, keratosis, rosacea, basal cell carcinoma, warts and cold-sore.

What is claimed is:

1. A composition comprising:

a) a crosslinked hydrophilic polymer obtained by reacting a hydrophilic polymer containing secondary or tertiary amino functional groups with a crosslinking agent which contains at least two epoxide functional groups, wherein the hydrophilic polymer containing secondary or tertiary amino functional groups is a random copolymer of Formula I, Formula I

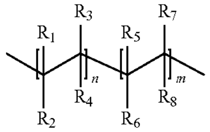

wherein n and m are independently selected from an integer from 100 to 50,000;

$R_1$, $R_2$, $R_4$, $R_5$, $R_6$ and $R_8$ are each independently selected from —H, —OH and $C_1$-$C_6$ alkyl optionally substituted by at least one hydroxyl group;

$R_3$ is selected from:
(i) —OH,
(ii) N-lactam,
(iii) —$COOR_9$, wherein $R_9$ is selected from —H, $C_1$-$C_6$ alkyl optionally substituted by at least one group selected from a hydroxyl group and —$(CH_2—CH_2—O)_p$—H wherein p is an integer from 1 to 10,
(iv) —$CONR_{10}R_{11}$, wherein $R_{10}$ and $R_{11}$ are independently selected from —H, $C_1$-$C_6$ alkyl optionally substituted by at least one group selected from a hydroxyl group and $(CH_2—CH_2—O)_p$—H wherein p is an integer from 1 to 10,
(v) —$NHCOR_{12}$, wherein $R_{12}$ is selected from $C_1$-$C_6$ alkyl optionally substituted by at least one group selected from a hydroxyl group and —$(CH_2—CH_2—O)_p$—H wherein p is an integer from 1 to 10, and
(vi) —$(CH_2—CH_2—O)_p$—H wherein p=1-10; and
$R_7$ is selected from:
(i) —$COOR_{13}$, wherein $R_{13}$ is $C_1$-$C_6$ alkyl substituted by at least one amino functional group,
(ii) —$CONR_{14}R_{15}$, wherein $R_{14}$ is $C_1$-$C_6$ alkyl substituted by at least one amino functional group and $R_{15}$ is selected from —H, $C_1$-$C_6$ alkyl optionally substituted by at least one group selected from a hydroxyl group, an amino functional group and —$(CH_2—CH_2—O)_p$—H wherein p=1-10, and
(iii) —$NHCOR_{14}$, wherein $R_{14}$ is selected from $C_1$-$C_6$ alkyl optionally substituted by at least one group selected from a hydroxyl group and —$(CH_2—CH_2—O)_p$—H wherein p is an integer from 1 to 10; and
b) a swelling agent.

2. The composition according to claim 1, wherein the molar percentage of the monomers in the hydrophilic polymer that contain an amino functional group is from 1% to 60%.

3. The composition according to claim 1, wherein the hydrophilic polymer containing amino functional groups is selected from poly(2-hydroxyethyl methacrylate-co-2-aminoethyl methacrylate), poly(acrylamide-co-2-aminoethyl methacrylate), poly(2-hydroxyethyl methacrylate-co-2-dimethylaminoethyl methacrylate), poly(1-vinylpyrrolidone-co-2-dimethylaminoethyl methacrylate), poly(acrylamide-co-2-dimethylaminoethyl methacrylate), poly(vinyl alcohol-co-n-[3-(dimethylamino)propyl] methacrylamide), and poly (acrylamide-co-3-dimethylaminopropyl methacrylamide).

4. The composition according to claim 1, wherein the crosslinking agent is selected from $C_4$-$C_{12}$ alkyl diepoxides, di-glycidyl ethers, tri-glycidyl ethers, poly-glycidyl ethers, and tris(2,3-epoxypropyl) isocyanurate.

5. The composition according to claim 4, wherein the crosslinking agent is selected from the group consisting of ethyleneglycol diglycidyl ether, glycerol diglycidyl ether, butanediol diglycidyl ether, diethylene glycol diglycidyl ether, hexanediol diglycidyl ether, neopentyl glycol diglycidyl ether, glycerol triglycidyl ether, glycerol polyglycidyl ether, trimethololpropane polyglycidyl ether, pentaerythritol polyglycidyl ether, polyethylene glycol diglycidyl ether, polypropylene glycol diglycidyl ether, sorbitol polyglycidyl ether, polyglycerol polyglycidyl ether, and combinations thereof.

6. The composition according to claim 1, wherein the swelling agent is selected from the group consisting of water, monohydric alcohols, polyhydric alcohols, ethoxylated polyhydric alcohols, methyl ethers of ethoxylated polyhydric alcohols, and combinations thereof.

7. The composition according to claim 1, wherein the swelling agent is selected from the group consisting of propylene glycol, dipropylene glycol, polyethylene glycol of molecular weight between 200 and 600, glycerol, diglycerol, triglycerol, tetraglycerol, and combinations thereof.

8. The composition according to claim 1, further comprising at least one compound selected from:
c) a modifying polymer compatible with the swelling agent, and
d) an active pharmaceutical ingredient.

9. The composition according to claim 8, comprising:
a) from 5% to 50% by weight of cross-linked hydrophilic polymer containing amino functional groups,
b) from 40% to 70% by weight of swelling agent, and optionally at least one further compound selected from
c) from 1% to 10% by weight of modifying polymer compatible with the swelling agent, and
d) from 0.5% to 25% by weight of active agent.

10. The composition according to claim 8, comprising an antimicrobial.

11. The composition according to claim 1, wherein the composition is a hydrogel.

12. The composition according to claim 1, wherein the composition is transparent and, optionally, colorless.

13. The composition according claim 1, wherein the composition is adhesive.

14. The composition according to claim 1, wherein:
the hydrophilic polymer containing amino functional groups is selected from poly(2-hydroxyethyl methacrylate-co-2-aminoethyl methacrylate), poly(acrylamide-co-2-aminoethyl methacrylate), poly(2-hydroxyethyl methacrylate-co-2-dimethylaminoethyl methacrylate), poly(1-vinylpyrrolidone-co-2-dimethylaminoethyl methacrylate), poly(acrylamide-co-2-dimethylaminoethyl methacrylate), poly(vinyl alcohol-co-n-[3-(dimethylamino)propyl] methacrylamide) and poly(acrylamide-co-3-dimethylaminopropyl methacrylamide);
the crosslinking agent is selected from $C_4$-$C_{12}$ alkyl diepoxides, di-glycidyl ethers, tri-glycidyl ethers, poly-glycidyl ethers, and tris(2,3-epoxypropyl) isocyanurate; and
the swelling agent is selected from the group consisting of water, monohydric alcohols, polyhydric alcohols, ethoxylated polyhydric alcohols, methyl ethers of ethoxylated polyhydric alcohols, and combinations thereof.

15. The composition according to claim 14, wherein the composition is an adhesive, transparent and, optionally, colorless, hydrogel.

16. The composition according to claim 10, wherein the antimicrobial is chlorhexidine gluconate.

17. A skin-contact medical article selected from the group consisting of a wound-dressing, a securement dressing, a sealant, a plaster and a patch, the article comprising the composition according to claim 1.

18. A method for obtaining a composition according to claim 1, the method comprising:
(i) mixing in the presence of a volatile solvent: a) a hydrophilic polymer containing secondary or tertiary amino functional groups, b) a swelling agent, c) a crosslinking agent which contains at least two epoxide functional groups,
(ii) subjecting the mixture at a temperature from 40 to 100° C. during 1 to 24 h, and optionally
(iii) placing in an aqueous solution for swelling.

19. A skin-contact medical article selected from the group consisting of a wound-dressing, a securement dressing, a sealant, a plaster and a patch, comprising the composition according to claim 14.

20. A method for obtaining a composition according to claim 8, the method comprising:

(i) mixing in the presence of a volatile solvent: a) a hydrophilic polymer containing secondary or tertiary amino functional groups, b) a swelling agent, c) a crosslinking agent which contains at least two epoxide functional groups, and optionally at least one further compound selected from d) a modifying polymer compatible with the swelling agent, and e) an active pharmaceutical ingredient, (ii) subjecting the mixture at a temperature from 40 to 100° C. during 1 to 24 h, and optionally (iii) placing in an aqueous solution for swelling.

* * * * *